United States Patent [19]

Kantrowitz et al.

[11] Patent Number: 4,733,652
[45] Date of Patent: Mar. 29, 1988

[54] INTRA-AORTIC BALLOON

[75] Inventors: Adrian Kantrowitz, Pontiac; Paul S. Freed, Bloomfield Hills; Avi Bar-Lev, Farmington Hills, all of Mich.; Sadahiko Mushika, Tokyo; Akira Suzuki, Nishio, both of Japan

[73] Assignee: Aisin Seiki Kabushiki Kaisha, Akira, Japan

[21] Appl. No.: 73,843

[22] Filed: Jul. 15, 1987

Related U.S. Application Data

[63] Continuation of Ser. No. 815,030, Dec. 31, 1985, abandoned.

[51] Int. Cl.$^4$ .............................................. A61B 19/00
[52] U.S. Cl. ................................. 128/1 D; 128/672; 604/96
[58] Field of Search .......................... 604/96, 43–45; 128/1 D, 344, 748, 786, 672, 675, 646, 656

[56] References Cited

U.S. PATENT DOCUMENTS

| | | | |
|---|---|---|---|
| 3,081,765 | 3/1963 | Kompelien | 128/344 |
| 3,533,403 | 10/1970 | Woodson . | |
| 3,553,625 | 1/1971 | Stedman . | |
| 3,585,983 | 6/1971 | Kantrowitz | 128/1 D |
| 3,692,018 | 9/1972 | Goetz et al. . | |
| 3,707,960 | 1/1973 | Freed | 128/1 D |
| 3,896,803 | 7/1975 | Mason | 604/44 |
| 3,913,565 | 10/1975 | Kawahara | 604/96 |
| 4,014,317 | 3/1977 | Bruno . | |
| 4,024,873 | 5/1977 | Antoshkiw et al. . | |
| 4,077,394 | 3/1978 | McCurdy | 128/1 D |
| 4,148,319 | 4/1979 | Kasper et al. | 604/96 |
| 4,191,193 | 3/1980 | Seo . | |
| 4,244,362 | 1/1981 | Anderson . | |
| 4,274,423 | 6/1981 | Mizuno et al. . | |
| 4,362,150 | 12/1982 | Lombardi, Jr. et al. | 128/1 D |
| 4,456,000 | 6/1984 | Schjeldahl et al. . | |
| 4,552,127 | 11/1985 | Schiff | 604/96 |
| 4,569,332 | 2/1986 | Schiff et al. | 128/1 D |

FOREIGN PATENT DOCUMENTS

| | | |
|---|---|---|
| 439636 | 6/1912 | France . |
| 1566674 | 5/1980 | United Kingdom . |
| 995751 | 4/1980 | U.S.S.R. . |

*Primary Examiner*—Stephen C. Pellegrino
*Attorney, Agent, or Firm*—Finnegan, Henderson, Farabow, Garrett & Dunner

[57] ABSTRACT

An intra-aortic balloon pump apparatus includes a first catheter one end of which is secured to a connector having a gas supply port, a balloon one end of which is secured to the distal end of the first catheter, a central tubular member the distal end of which projects from the distal end of the first catheter and to which the distal end of the balloon is fixedly secured, a second catheter freely insertable into the central tubular member and having a distal end provided with an arterial pressure transduceer, and a second connector to which the other end of the second catheter is secured for feeding a signal from the pressure transducer to the outside of the apparatus. After the balloon, central tubular member and first catheter are placed into the aorta, the second catheter having the pressure transducer at its distal end is inserted through the interior of the central tubular member into the aorta.

5 Claims, 3 Drawing Figures

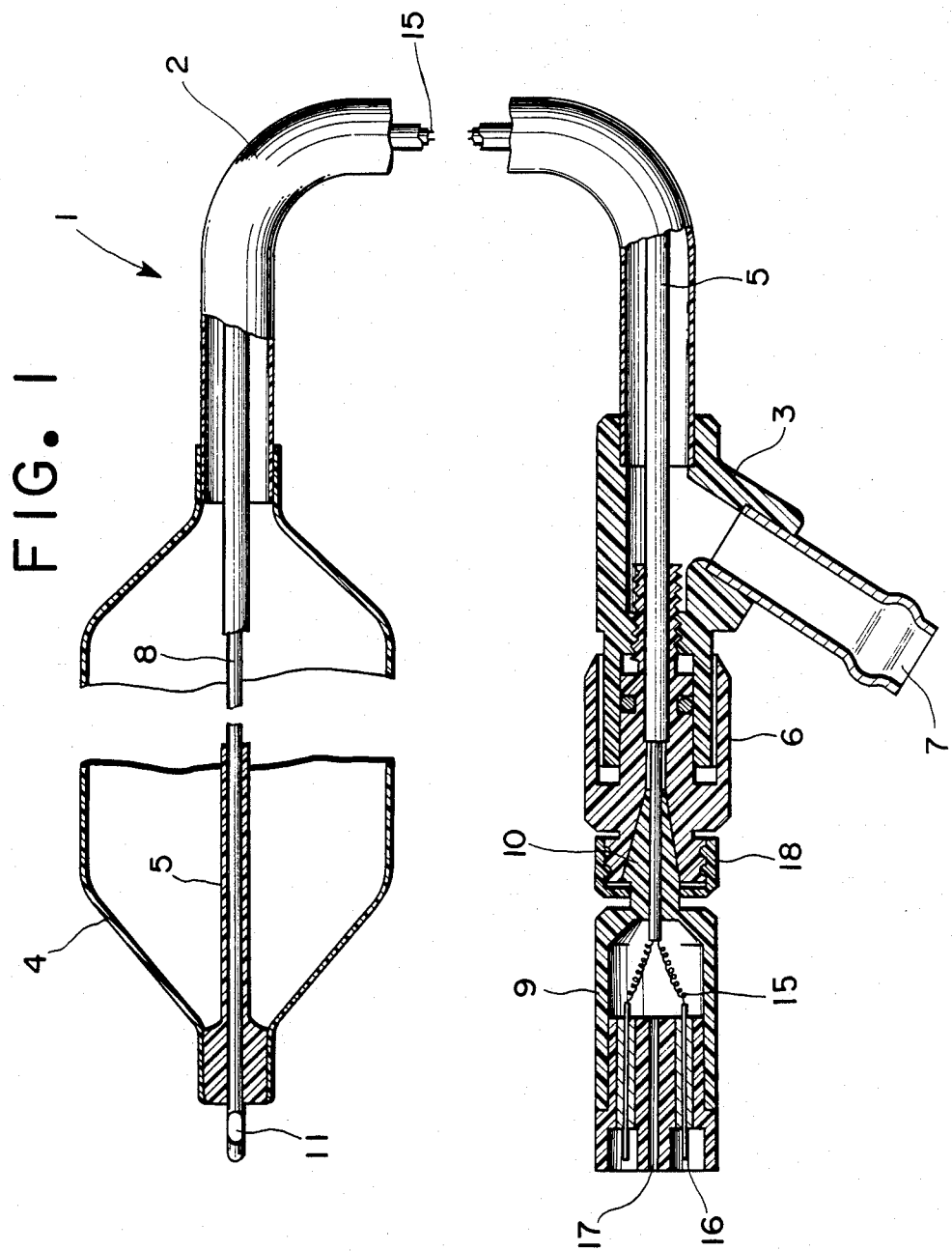

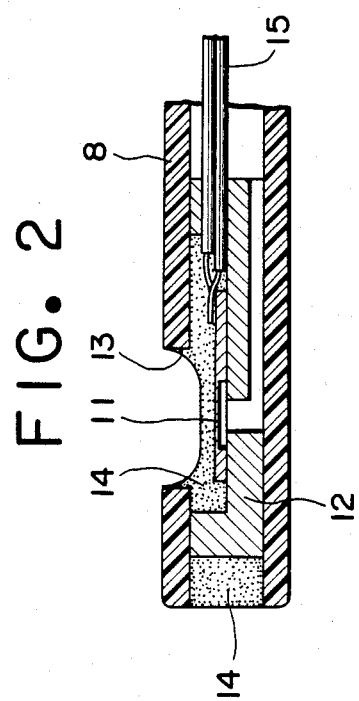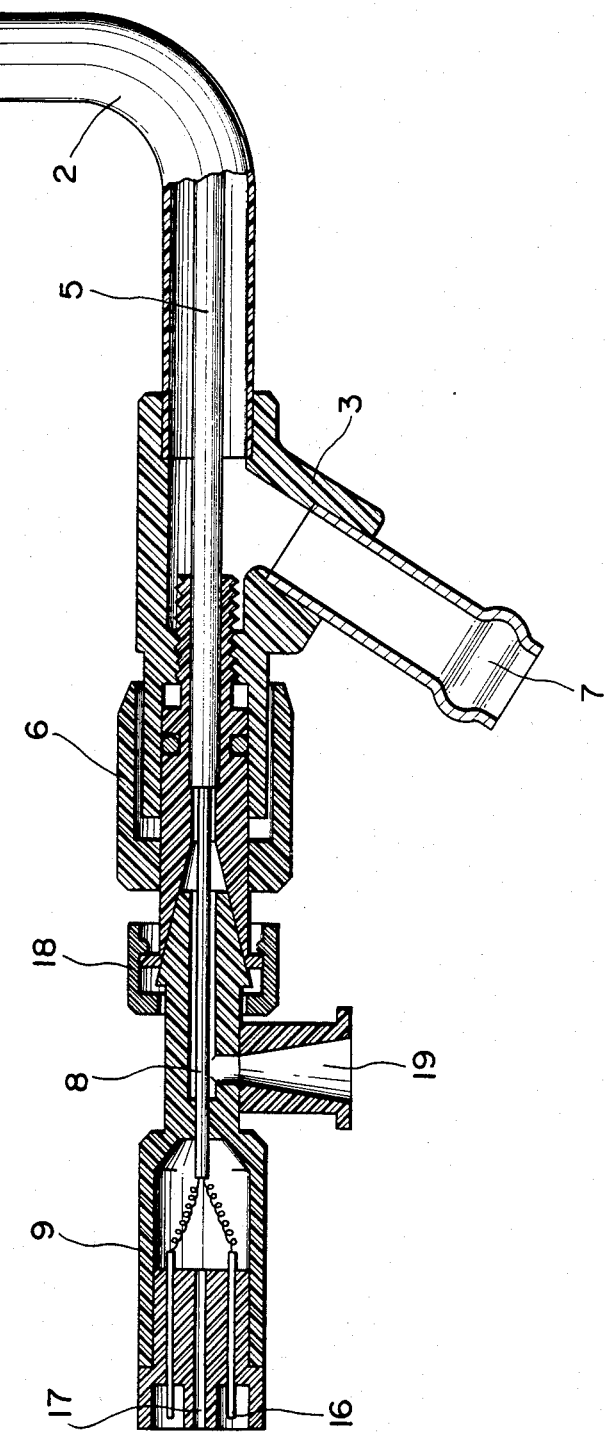

INTRA-AORTIC BALLOON

This application is a continuation, of application Ser. No. 815,030, filed Dec. 31, 1985 abandoned.

BACKGROUND OF THE INVENTION

This invention relates to an intra-aortic balloon pump apparatus and, more particularly, to an intra-aortic balloon pump apparatus that makes it convenient to introduce a pressure transducer into the aorta.

An intra-aortic balloon pump apparatus basically comprises a catheter through which a fluid such as helium gas is passed, and a balloon attached to the distal end of the catheter which is cyclically inflated by feeding helium gas into the balloon from an external source via the catheter. The apparatus is inserted into the patient, usually through the femoral artery, either percutaneously or through an incision, and advanced until it lies within the thoracic aorta. There it is made to inflate and deflate synchronous with the heart so as to reduce the load on the left ventricle and increase the amount of coronary blood flow.

An example of an intra-aortic balloon pump apparatus capable of being inserted into a living body by percutaneous introduction (Seldinger technique) is disclosed in the specification of U.S. Pat. No. 4,362,150.

During use of an intra-aortic balloon pump apparatus, an electro-cardiogram and an arterial pressure signal are utilized to determine the time of inflation and deflation of the balloon. An example of such an apparatus is disclosed in the specification of U.S. Pat. No. 3,585,983. Here a pressure transducer is disposed at the distal end of the balloon and a signal produced by the pressure transducer is led out from the patient's body through the catheter. This conventional arrangement has the limitation that the balloon apparatus cannot be introduced into the patient percutaneously and, hence, the apparatus is limited to inhospital use.

A different arrangement is set forth in the specification of U.S. Pat. No. 4,077,394. Here a small tube leads from the tip of the balloon through the catheter, feeding aortic pressure to a sensor located externally to the patient. However, this apparatus possesses the same drawback mentioned above, namely the fact that percutaneous introduction is not feasible.

If the method of measuring aortic pressure described in U.S. Pat. No. 4,077,394 were to utilize the central tube mentioned in U.S. Pat. No. 4,362,150, then the apparatus could be applied in the same manner. However, the system still would be prone to considerable external noise and distortion of the pressure signal which would make computerized recognition of the pressure signal unreliable.

SUMMARY OF THE INVENTION

Accordingly, an object of the present invention is to enable the accurate measurement of central aortic pressure by an intra-aortic balloon pump apparatus which is also capable of being introduced percutaneously.

According to the present invention, the foregoing objects are attained by providing an intra-aortic balloon pump apparatus comprising: a first connector having a gas supply port; a tubular first catheter having a proximate end and a distal end, the proximate end being fixedly secured to the first connector; a balloon having a proximate end and a distal end, the proximate end being fixedly secured to the distal end of the catheter; a central tubular member defining therein a passageway extending the length thereof and having a distal end projecting from the distal end of the first catheter, the distal end of the balloon being fixedly secured to the distal end of the central tubular member; a second catheter freely insertable into the central tubular member and having a distal end and a proximate end, the distal end being provided with a pressure transducer; and a second connector to which the proximate end of the second catheter is fixedly secured for feeding a signal from the pressure transducer to the outside of the apparatus; the second catheter being inserted into an aorta through the passage in the central tubular member after the balloon, the central tubular member and first catheter are inserted into the aorta, the pressure transducer projecting into the aorta from the distal end of the central tubular member.

In an embodiment of the present invention, the second catheter of the intra-aortic balloon pump apparatus comprises a stainless steel tube and leads from the pressure transducer are extended to the second connector by being passed through the interior of the second catheter. In another embodiment, the second connector is provided with a medical fluid port communicating with the aorta through a passageway defined between the central tubular member and the second catheter.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 1 is a side view, partially shown in section, illustrating an embodiment of an intra-aortic balloon pump apparatus according to the present invention;

FIG. 2 is an enlarged sectional view illustrating a pressure transducer included in the apparatus of FIG. 1; and FIG. 3 is a side view, partially shown in section, illustrating another embodiment of an intra-aortic balloon pump apparatus according to the present invention.

DESCRIPTION OF THE PREFERRED EMBODIMENT

An embodiment of an intra-aortic balloon pump apparatus according to the present invention will now be described with reference to FIGS. 1 and 2. The apparatus, shown generally at numeral 1, includes a tubular first catheter 2 having a proximate end joined to a Y-shaped connector 3 and a distal end supporting the proximate end of the balloon 4 air-tightly. A central tubular member 5 extends through the interior of the first catheter 2 and has a distal end of comparatively larger diameter projecting from the distal end of first catheter 2 and air-tightly supporting the distal end of the balloon 4.

The central tubular member 5 has a proximate end fixedly secured to a rotary member 6 having a portion in threaded engagement with the connector 3. Turning the rotary member 6 with respect to the connector 3 rotates the central tubular member 5 so that the balloon 4 may be wrapped around the central tubular member 5 by rotating the same in one direction and unwrapped from the central tubular member 5 by rotating same in the opposite direction. The connector 3 has a port 7 from which a fluid such as helium gas is introduced from an external source, not shown. The gas is fed from connector 3 into the balloon 4 through a passageway defined between the inner surface of first catheter 2 and the outer surface of central tubular member 5, whereby the balloon 4 is made to inflate. Withdrawing the gas from the balloon through the same passageway causes the balloon to deflate.

A tubular second catheter 8, the diameter whereof is smaller than that of the first catheter 2, is capable of being passed through the passageway of the central tubular member 5 and has a distal end that projects from the distal end of the central tubular member 5. The second catheter 8 has a proximate end secured to a second connector 9. The second connector 9 has a tapered distal end portion 10 lockably fitted into a tapered bore formed inside the rotary member 6. A knob 18 is provided for releasably locking the second connector 9 to the rotary member 6.

Disposed on the distal end portion of the second catheter 8 is a pressure transducer 11, as shown in FIG. 2. The transducer 11 is adapted to sense aortic pressure and produce a signal indicative thereof. Specifically, the pressure transducer 11 is attached to a metal block 12 secured to the inner wall surface of the second catheter 8 so as to face a pressure detection opening 13 formed in a portion of the catheter wall. The tip of the second catheter 8 and the pressure detection opening 13 are filled with silicone material 14 for holding the metal block 12 and, hence, the pressure transducer 11, in place inside the distal end of the second catheter 8. The pressure transducer 11 has lead wires 15 which pass through the interior of the second catheter 8 and extend into the second connector 9, where they are electrically connected to terminals 16 provided inside the connector 9. The terminals 16 of the second connector 9 thus receive the aortic pressure signal from the pressure transducer 11. The second connector 9 is in turn connected to electronic circuitry, not shown, the function whereof is described hereinbelow. The second connector 9 is formed to include an air passage 17 for communicating the external atmosphere with the underside of the pressure transducer 11, i.e., the side of the transducer facing away from the pressure detection opening 13, so that this side of the transducer is maintained at a constant pressure at all times. In a preferred embodiment, the second catheter 8 comprises a stainless steel tube, the outer diameter whereof is not more than 0.8 mm.

To use the intra-aortic balloon pump apparatus 1 shown in FIG. 1, first a guide wire, now shown, is introduced into the aorta via the patient's femoral artery as by the Seldinger technique until the leading end of the guide wire reaches the aortic arch. Next, the other end of the guide wire is inserted into the distal end of the central tubular member 5, into which the second catheter 8 has not yet been introduced. The central tubular member 5, with the balloon 4 wrapped around it, is then advanced together with the first catheter 2 into the aorta while being guided along the guide wire. When these have reached a predetermined position inside the aorta, the guide wire is withdrawn from the patient's body through proximate end of the central tubular member.

Next the distal end of the second catheter 8 is inserted into the central tubular member 5 and advanced while manipulating the connector 9 to which the second catheter 8 is affixed, until the pressure transducer 11 at the distal end of the second catheter is made to project into the aorta from the distal end of the central tubular member 5. The tapered distal end portion 10 of second connector 9 is then brought into abutting contact with the rotary member 6 and the knob 18 is turned to lock the second connector 9 and rotary member 6 together. Now the rotary member 6 is turned to unwrap the balloon 4 from the central tubular member 5, thereby setting the balloon at the predetermined position in the aorta. The connector 9 is connected to the aforementioned electronic circuit, which thus receives the aortic pressure signal from the pressure transducer 11 at the distal end of the second catheter 8 via the lead wires 15 and terminals 16 and calculates the appropriate counterpulsation timing in accordance with the aortic pressure signal.

The intra-aortic balloon apparatus 1 is capable of being adapted to function without requiring the step of inserting the second catheter 8. In such an arrangement, the tapered distal end portion 10 of the second connector 9 may be replaced by a tapered plug engaged with the rotary member 6.

Another embodiment of the invention is illustrated in FIG. 3. Here a portion of the second connector 9 is provided with a port 19 communicating with the aorta through a passageway defined between the central tubular member 5 and second catheter 8. The port 19 is useful for feeding a medical fluid into the aorta during the operation of the intra-aortic balloon pump apparatus 1. The structure is the same as that shown in FIG. 1 in other respects and identical portions are designated by like reference characters and need not be described again.

It should be clear from the above description that, according to the present invention, the passageway defined inside the central tubular member has multiple uses, it is used for introducing the balloon pump into the patient's aorta along the guide wire inserted beforehand, and for the placement of the second catheter having the pressure transducer provided thereon close to the patient's heart. This makes it possible to accurately measure arterial pressure and, hence, to achieve counterpulsation timing far more precise than that obtainable in the prior art.

As many apparently widely different embodiments of the present invention can be made without departing from the spirit and scope thereof, it is to be understood that the invention is not limited to the specific embodiments thereof except as defined in the appended claims.

What we claim is:

1. An intra-aortic balloon apparatus comprising:
    a first connector having a gas supply port;
    a tubular first catheter having a proximate end and a distal end, the proximate end being fixedly secured to said first connector;
    a balloon having a proximate end and a distal end, the proximate end being fixedly secured to the distal end of said first catheter;
    a central tubular member inserted in said first catheter and defining therein a passageway extending the length thereof and having a distal end projecting from the distal end of said first catheter and a proximate end extending through said first connector, the distal end of said balloon being fixedly secured to the distal end of said central tubular member;
    a second catheter freely insertable into the passageway of said central tubular member and having a distal end, a proximate end, and a length between said distal end and proximate ends thereof being longer than that of said central tubular member, the distal end being provided with a pressure transducer;

a second connector having a proximate end to which the proximate end of said second catheter can be fixedly secured for feeding a signal produced by the pressure transducer to the outside of the apparatus;

means for sealing said passageway in said central tubular member to retain fluid within said passageway;

said balloon, said central tubular member and said first catheter being insertable into the aorta of a patient; and said second catheter being insertable into said passageway in said central tubular member with said pressure transducer being projectable into the aorta from the distal end of said central tubular member.

2. The apparatus according to claim 1, wherein said second catheter comprises a stainless steel tube, said pressure transducer having lead wires extending through the interior of said second catheter to said second connector.

3. The apparatus according to claim 1, wherein said second connector is provided with a port communicating with the aorta through the passageway in said central tubular member.

4. The apparatus according to claim 1, wherein said sealing means comprises a rotary member fixedly secured to said proximate end of said central tubular member and having a portion engaged with said second connector.

5. The apparatus according to claim 4, wherein said portion of said rotary member is formed with a tapered bore and said second connector includes a tapered distal end portion for lockably fitting in said tapered bore.

* * * * *